United States Patent
Tennby et al.

(10) Patent No.: US 6,471,804 B1
(45) Date of Patent: Oct. 29, 2002

(54) METHOD AND DEVICE FOR FIXING PIECES OF MATERIAL ON A CONTINUOUS WEB

(75) Inventors: Anders Tennby, Kungsbacka (SE); Thomas Åberg, Göteborg (SE); Bo Thornström, Harestad (SE); Kenneth Henriksson, Mölndal (SE); Roy Hansson, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/743,269

(22) PCT Filed: Jun. 29, 1999

(86) PCT No.: PCT/SE99/01169

§ 371 (c)(1),
(2), (4) Date: Mar. 29, 2001

(87) PCT Pub. No.: WO00/02727

PCT Pub. Date: Jan. 20, 2000

(30) Foreign Application Priority Data

Jul. 8, 1998 (SE) ............................................ 9802456-5

(51) Int. Cl.⁷ ............................................... B32B 31/00
(52) U.S. Cl. ..................... 156/73.1; 156/256; 156/290; 156/517; 156/554; 156/580.1; 156/580.2
(58) Field of Search ............................... 156/73.1, 250, 156/256, 290, 510, 516, 517, 554, 580.1, 580.2

(56) References Cited

U.S. PATENT DOCUMENTS 4,823,783 A * 4/1989 Willhite, Jr. et al. ....... 128/156
5,059,277 A   10/1991 Willhite, Jr. et al.
5,817,199 A * 10/1998 Brennecke et al. ........ 156/73.1

FOREIGN PATENT DOCUMENTS

| GB | 2 145 970 | 4/1985 |
| GB | 2 335 627 | 9/1999 |
| WO | 97/23340 | 7/1997 |
| WO | 98/28123 | 7/1998 |

* cited by examiner

*Primary Examiner*—James Sells
(74) *Attorney, Agent, or Firm*—Burns, Doane, Swecker & Mathis, L.L.P.

(57) ABSTRACT

The invention relates to a device and a method for producing a material laminate (1) by fixing pieces of material (2) at a given distance from one another on a first continuously advanced material web (4). The invention is characterized in that the pieces of material (2) are cut from a second continuous web (7) in a first station (3) and are conveyed via a transport device (10) to the first web (4), to which the piece of material (2) is attached by means of ultrasonic welding over a limited attachment area (5) on the pieces of material (2), and the pieces of material (2) are subsequently fixed to the material web (4) by ultrasonic welding in a second station (6). The second station comprises an ultrasonic horn (18) at a fixed distance from a stay (19) designed as a rotating drum with a patterned outer surface.

18 Claims, 3 Drawing Sheets

METHOD AND DEVICE FOR FIXING PIECES OF MATERIAL ON A CONTINUOUS WEB

TECHNICAL FIELD

The present invention relates to a method and a device for fixing fibrous pieces of material made of porous and springy material at a given distance from one another on one or more continuously advanced material webs and, for joining together, establishing an optional pattern on the piece of material, preferably for production of a material laminate for use in absorbent products. The absorbent products can consist of nappies, baby pants, incontinence pads, sanitary towels, panty liners or the like. The invention can also be used within other areas in which one or more shorter pieces of material are to be fixed on one or more continuous webs.

BACKGROUND

It is previously known to fix pieces of material on a web by gluing. The gluing procedure has been found to have considerable disadvantages such as, for example, the handling of additional material which also involves undesirable costs. Other disadvantages in the process using glue are that glue residues are deposited in inappropriate places in the equipment and thus create problems, and also that the use of glue involves extra cost, and glue layers in a liquid-transporting material laminate impair the prerequisites for liquid flow.

It is also known to join one or more continuous webs together by means of ultrasound. This is disclosed in, for example, WO 97/23340 which describes the use of ultrasonic horns in combination with rotating stays for joining continuous webs together in a given pattern, where the purpose of the pattern is to make possible intermittent joining together of two or more continuous webs. This known arrangement is not suitable for fixing short pieces of material to a continuous web.

The object of the invention and its most important characteristics.

The object of the invention is to solve the problems associated with the techniques indicated above and to make it possible to use ultrasonic welding for fixing pieces of material on a continuous web. Above all, the invention makes possible rapid, cost-saving and simple adjustments for adaptation to changed circumstances, for example a change of material or the exchange of various parts of the equipment, and adjustments in the event of patterns being exchanged. Moreover, the invention results in short operational stoppages for service and maintenance.

According to the invention, this is achieved on the one hand by a method in which each piece of material is attached to the continuous web by means of ultrasound in a first station, after which the piece of material is fixed by its entire contact surface by means of ultrasound in a second station, and on the other hand by a device consisting of a first station for attaching the piece of material to the continuous web and a second station in which the piece of material is fixed over its entire surface to the continuous web.

The invention results in the advantages that the material can be produced without the use of glue and thus the costs and service requirements are reduced.

The invention also affords the advantage that, by means of continuous energy supply to ultrasonic horns, pieces of material are fixed to a continuous web and at the same time a pattern as described in, for example, Patent Application SE 9801038-2 is obtained.

The invention is not to be construed as being limited to the details of the device and method described below, or to what is illustrated in the figures.

DESCRIPTION OF EMBODIMENTS

Figure 1:
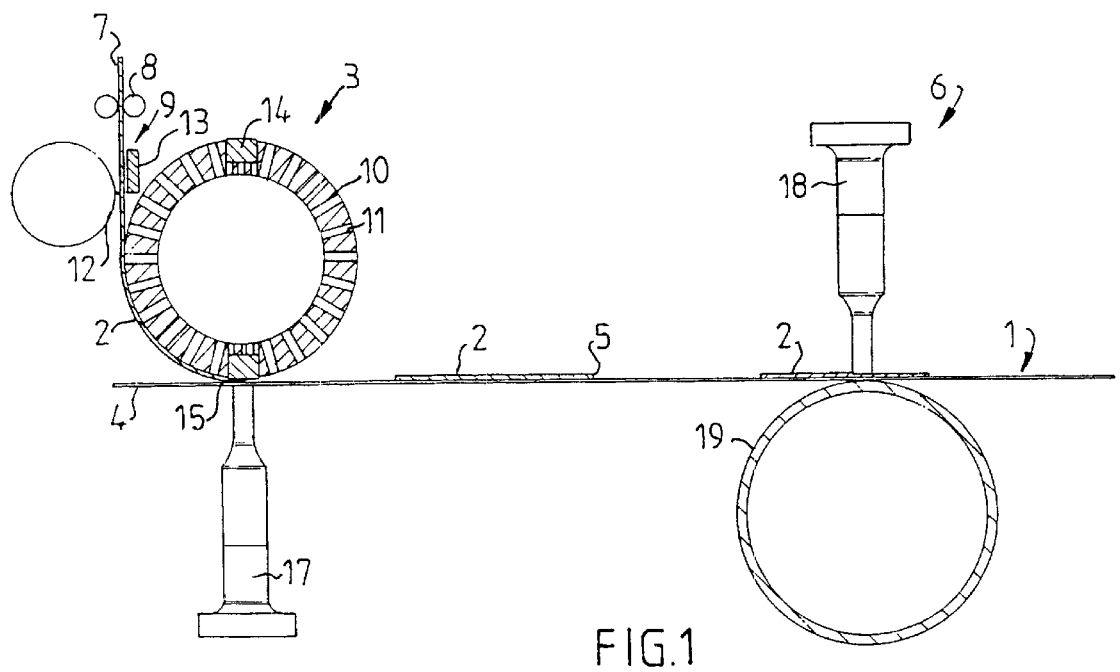
FIG. 1 shows a side view of processing equipment according to a first embodiment of the invention.

FIG. 1 illustrates processing equipment according to an embodiment of the invention for producing a material laminate 1, in which a piece of material 2 is in a first station 3 placed in the desired position on a first continuous material web 4 and is attached in this position by ultrasonic welding in a pattern within at least an area 5 which covers a part of the contact surface of the piece of material 2 against the material web 4, and is subsequently fixed on the material web 4 by ultrasonic welding in a second station 6 with a pattern which covers essentially the entire contact surface against the material web, by means of which a material laminate 1 is formed for use in absorbent products.

The continuous and continuously advanced first continuous web 4 can constitute, for example, an outer layer in an absorbent product and then usually consists of a thin material of the nonwoven type. The first material web 4 can consist of nonwoven material containing at least 5% thermoplastic fibres, usually more than 40% thermoplastic fibres. All thermofibres commonly used in the branch which can be softened and/or fused when subjected to ultrasonic energy can be used in the invention described here. The first material web 4 which is fed into the machine can consist of a prefabricated material and can be produced by a number of different methods, for example by carding or spinning a fibre web which is subsequently bound with a binder. What is known as the melt-blown technique can also be used in order to lay short fibres down in the form of a fibre mat. Heat-fusible components in the material can also be used for binding by means of ultrasound. The material web 4 can also consist of a composite nonwoven material. The substance of the material in the first material web 4 for use according to the invention is usually between 10 and 80 $g/m^2$, preferably between 10 and 50 $g/m^2$.

The pieces of material 2 are attached to the material web 4 in the first station 3 at a given distance from one another, and they are produced from a second continuous material web 7. The material in this web can consist of the same material as that in the first material web 4 or of a different material. The second continuous material web 7 can likewise consist of a number of webs lying one on another and/or two or more, preferably three, parallel webs with the same or a different material composition. Material for the pieces of material 2 which is especially suitable for use in absorbent products is wadding material with a substance greater than 10 $g/m^2$, preferably between 10 and 250 $g/m^2$ or in particular between 20 and 100 $g/m^2$, consisting mainly of springy fibres and comprising thermoplastic material or at least a surface structure of thermoplastic material.

The second continuous material web 7 is fed continuously by feed rollers 8 at a feed speed which can be regulated in the conventional manner, by means of which the material web 7 is imparted a considerably reduced feed speed in relation to the first continuous material web 4. By suitable selection of the feed speed of the second material web 7 and synchronization of the cutting unit 9, the distance between the pieces of material 2 when they are positioned on the first material web 4 can be defined.

When the material in the second continuous material web 7 has been advanced by the feed rollers 8 to a given length, it will be arranged on the transport drum 10 over a part of the length of a piece of material 2. By creating a negative pressure in the transport drum, suction is generated through holes 11 in the outer surface of the transport drum 10, which suction ensures the continued transport of the second continuous material web 7 after the feed rollers 8. When the given length of a piece of material has been advanced, the material web is cut by a cutting unit 9 with a cutting tool in the form of a cutting roller 12 which interacts with a fixed or rotating stay 13, after which the transport speed of the piece of material 2 produced increases to the speed constituting the peripheral speed of the transport drum, which essentially corresponds to the speed of the first continuous web 4.

By means of fastening devices, easily exchangeable jaws 14 are mounted on the transport drum 10. These jaws are preferably made of a different type of material with superior wear and strength properties than the material in the rest of the outer surface of the transport drum. The jaws 14 can advantageously be made of metal, preferably hardened steel. The number of jaws 14 on the drum 10 can be one or more and depends on inter alia the interrelationship between the length of the pieces of material 2 and the diameter of the drum 10. The raised part of the pattern on the stay jaws 14 establishes binding points when the piece of material 2 is attached to the material web 4. The flexibility and softness of the material are retained to a high degree when the binding points account for 2–20% of the attachment area.

The jaws 14 are provided with a suitable raised pattern and also a number of through-holes, by means of which the negative pressure in the drum sucks the first end 15 of the piece of material 2 firmly against the jaw 14. The through-holes in the jaws 14 are located in suitable positions in relation to the selected pattern on that side of the jaw which constitutes a part of the periphery of the transport drum 10, while the holes in said periphery are independent of both the pattern defined at the time for welding by means of ultrasonic energy and the thickness of the material and its extent in the transverse direction of manufacture. The pattern depth of the jaws 14 for manufacturing material for absorbent products suitably varies between 0.3 mm and 1.5 mm and preferably 0.5 and 1.0 mm for thin material with a thickness of between 0.2 mm and 2.0 mm.

The jaws 14 on the transport drum 10 are arranged so that the radius R' from the centre of the drum to the patterned surface of the jaw is greater than the radius R" from said centre to the outer surface of the drum. The recommended magnitude of the difference (R'–R") can be expressed as (R'–R")≧1.5×the thickness of the material laminate 1.

Figure 2:
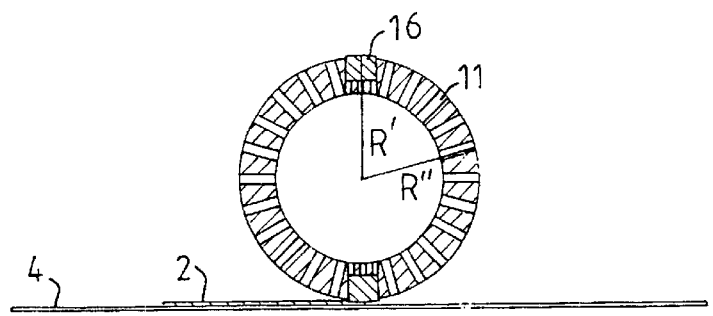
FIG. 2 shows a side view of a first welding station in the processing equipment according to FIG. 1.
Figure 3:
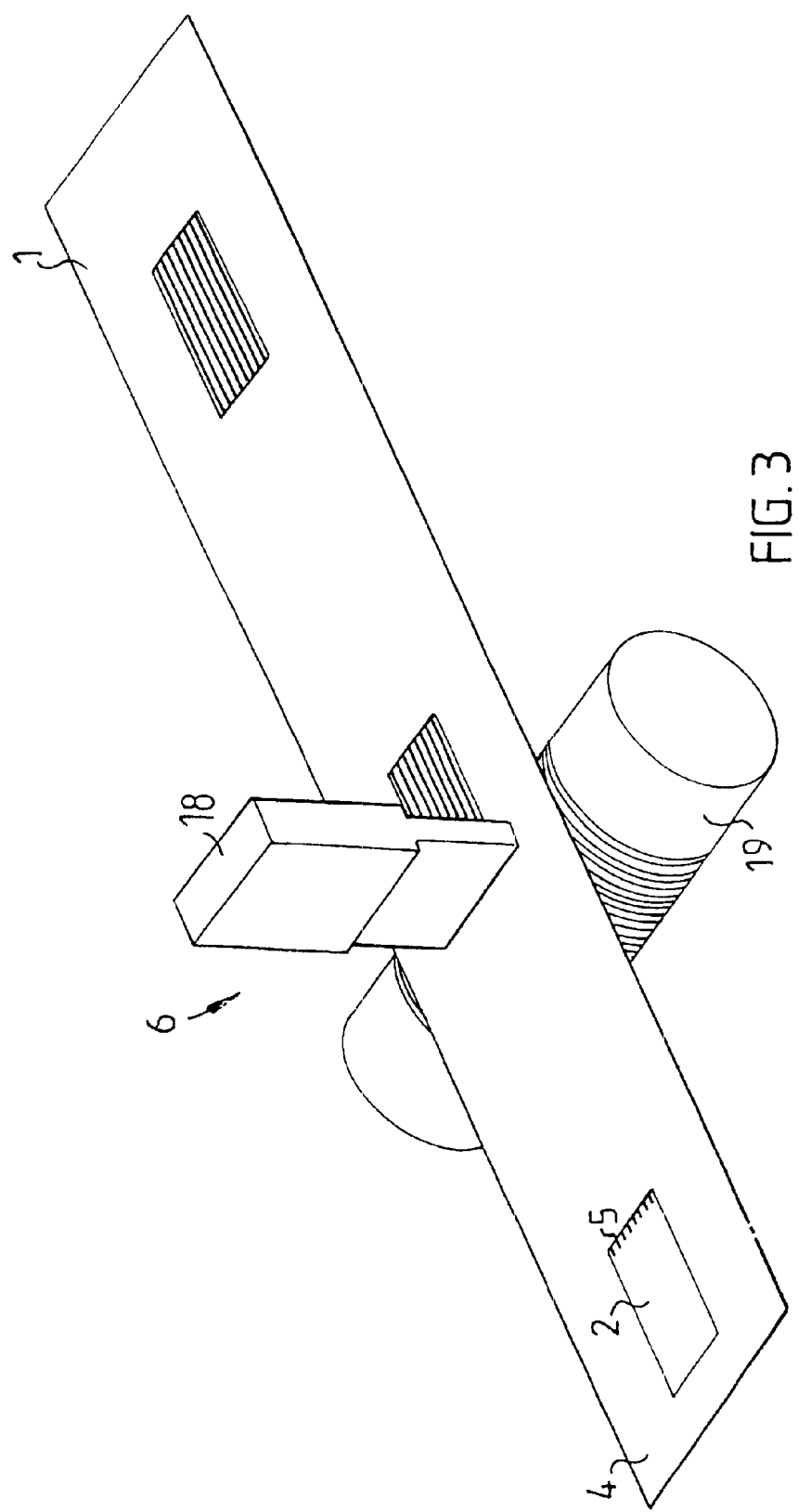
FIG. 3 shows a perspective diagram of a second welding station in the processing equipment according to FIG. 1.

The synchronization between the positions of the cutting roller 12 and the transport drum 10 at the time of cutting is selected so that the piece of material 2, on cutting in the cutting station 9, does not completely cover the jaw 14 over its extent in the machine direction, as can be seen from FIG. 2, and affords the great advantage that the requirement for precise control of the cutting roller 12 is reduced. The patterned surface 16 of the jaws 14 has an extent in the transverse direction of the machine which exceeds the width of the finally joined-together area 5 between the pieces of material 2 and the continuous web 4, which to some extent reduces the requirement for precise guidance of the material around an imaginary longitudinal centre line in the machine direction.

The peripheral speed of the transport drum 10 corresponds essentially to the linear speed of the material web 4 when the two materials 2, 4 meet. Attachment of the piece of material 2 to the web 4 is effected by ultrasonic energy generated by an ultrasonic horn 17 positioned on the other side of the material web 4 in relation to the transport drum 10 with the jaws 14 which constitute a stay for the ultrasonic horn 17 which is continuously fed with energy.

The prerequisite for attaching the first end 15 of the piece of material 2 to the material web 4 according to the present invention can be defined by the following parameters:

| | |
|---|---|
| Thickness of the first material web 4 = | A |
| Thickness of the second material web 7 = | B |
| Distance between ultrasonic horn 17 and stay/jaw 14 = | C |
| Width of the second material web 7 = | D |
| Smallest width of jaw 14, or width of ultrasonic horn 17 = width of the jaw 14 is constituted by its extent in the transverse direction of the device. | E |
| Extent of the jaw 14 in the machine direction = | F |
| Extent of the attachment area 5 in the machine direction = | G |

Using the definitions listed above, the following applies:

$A+B>C \quad F>G \quad D<E$

When the piece of material 2 is attached to the continuous material web 4 in one or more places over a part of its length, it is transported together with the material web 4 to the second station 6. This second station includes a second ultrasonic horn 18 and a stay in the form of a roll or drum 19 arranged on the opposite side of the web. The ultrasonic horn 18 is fed continuously with energy and is fixed during operation at a given distance from the stay roll 19. This position is defined in the same way as described above with regard to the ultrasonic horn in the first station 3.

The pattern on the stay 19 constitutes a surface structure on the outer surface, in which the appearance and depth of the pattern are defined on the basis of requirements relating to the appearance of the final material laminate. For material for absorbent products, where the first continuous material web 4 can consist of nonwoven with a thickness of less than 0.5 mm, the thickness is preferably within the range 0.2–0.5 mm, the pieces of material 2 can consist of wadding with a thickness of less than 2.0 mm, preferably within the range 0.5–2.0 mm. When materials of the type described are joined together, use is made of a pattern depth of 0.3–2.0 mm, preferably 0.5–1.0 mm. The raised part of the pattern on the stay 19 establishes binding points when the piece of material 2 is fastened to the material web 4. The flexibility and softness of the material are retained to a high degree when the binding points account for 2–20% of the attachment area. The extent of the pattern in the transverse direction on the stay 19 exceeds the width of the material laminate or has preferably greater width than the piece of material 2, resulting in precise guidance of the material web 4 in the transverse direction of the machine not being required. The ultrasonic horn 18 does not have to be wider than the patterned part of the stay 19.

Figure 4:
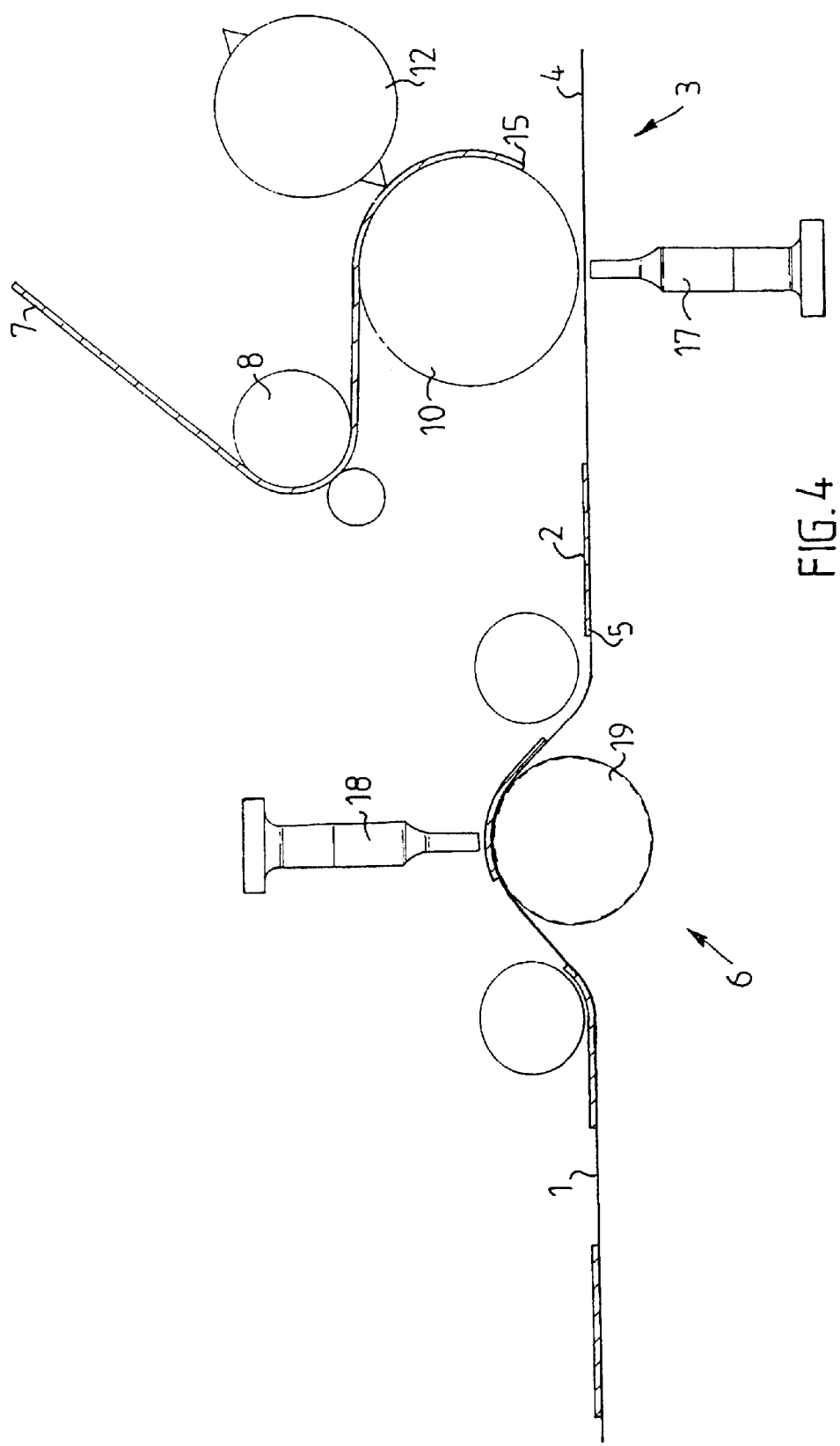
FIG. 4 shows a second embodiment of the first welding station with a combined drum for a stay during cutting and transport.

FIG. 4 shows a second embodiment which is characterized in that the cutting roller 12 in the cutting unit 9 works directly against the transport drum.

What is claimed is:

1. Method for fixing pieces of material at a given distance from one anothe,r on a continuously advanced material web, preferably for production of a material laminate for use in an absorbent product, characterized in that each piece of material is in a first station placed in the desired position on the material web and is attached in this position by ultrasonic welding in a pattern within at least an area which covers a part of the contact surface of the piece of material against the material web, and is subsequently fixed on the material web by ultrasonic welding in a second station with a pattern which covers essentially the entire contact surface against the material web.

2. Method according to claim 1, characterized in that the pieces of material are fed to the first station in the form of a second continuous web which is divided into separate pieces of material in the first station, which are placed in the desired position on the first continuous web.

3. Method according to claim 2, characterized in that the speed of the second continuous web is set lower than the speed of the first continuous web to such an extent that the desired distance between the pieces of material is obtained.

4. Method according to claim 1, characterized in that the ultrasonic welding in the first station and the second station is performed by ultrasonic horns which are fed continuously with energy.

5. Method according to claim 1, characterized in that the attachment of the piece of material in the first station is carried out in the front part of the piece of material, seen in the feed direction of the first continuous web.

6. Method according to claim 5, characterized in that the attachment has an extent in the machine direction of 3–24 mm, preferably 5–15 mm, from the front edge of the piece of material.

7. Method according to claim 4, characterized in that connection points are produced within the area of attachment in a pattern in which the connection points account for 2–20% of the attachment area.

8. Device for fixing pieces of material at a given distance from one another on a continuously advanced material web, preferably for production of a material laminate for use in an absorbent product, characterized by on the one hand a first station with an ultrasonic horn positioned on one side of the material web and a transport and stay device positioned on the opposite side of the material web and intended for placing a piece of material in the desired position on the material web and attaching the piece of material to the material web within a limited area in interaction with the ultrasonic horn, and on the other hand a second station with a second ultrasonic horn on one side of the material web and a stay device on the opposite side of the material web, which stay device is designed with a patterned surface which faces the material web and is intended, in interaction with the second ultrasonic horn, to fix the piece of material to the material web with the desired welding pattern which covers essentially the entire contact surface of the piece of material.

9. Device according to claim 8, characterized in that the stay device in the first station is mounted on the transport device.

10. Device according to claim 8, characterized in that the transport and stay device in the first station comprises a drum with internal negative pressure and through-holes in the outer surface.

11. Device according to claim 9, characterized in that the stay device in the first station has through-holes, the positioning of which is adapted to the desired attachment pattern, in order to secure the piece of material by means of the negative pressure in the drum.

12. Device according to claim 8, characterized in that the first station comprises a cutting unit with a cutting tool and a fixed or rotating stay for interaction with the tool.

13. Device according to claim 12, characterized in that the stay of the cutting unit is integrated into the transport and stay device.

14. Device according to claim 8, characterized in that the stay and the ultrasonic horn in the first station have an extent in the feed direction of the material web which is greater than the attachment produced.

15. Device according to claim 8, characterized in that the stay and the ultrasonic horn in the first station have an extent in the transverse direction of the material web which is greater than the extent of the piece of material in his direction.

16. Device according to claim 8, characterized in that the stay device for the ultrasonic horn in the second station consists of a cylindrical drum with a continuously patterned outer surface.

17. Device according to claims 8, characterized in that the stay device and the ultrasonic horn in the second station have an extent in the transverse direction of the machine which is greater than the extent of the piece of material in the same direction.

18. Device according to claims 8, characterized in that the pattern depth of the stay device in the first station and the second station is within the range 0.3–2.0 mm, preferably 0.5–1.0 mm.

* * * * *